United States Patent [19]

Burch

[11] Patent Number: 5,228,444

[45] Date of Patent: Jul. 20, 1993

[54] DEVICE FOR PRODUCING A GAS-LITE RADIONUCLIDE COMPOSITION

[75] Inventor: William M. Burch, Duffy, Australia

[73] Assignee: I. J. & L. A. Tetley Manufacturing Pty. Ltd., New South Wales, Australia

[21] Appl. No.: 661,664

[22] Filed: Feb. 27, 1991

Related U.S. Application Data

[63] Continuation of Ser. No. 462,303, Dec. 21, 1989, abandoned, which is a continuation of Ser. No. 251,930, Sep. 29, 1988, abandoned, which is a continuation of Ser. No. 784,847, Oct. 4, 1985, abandoned.

[30] Foreign Application Priority Data

Oct. 4, 1984 [AU] Australia .............................. PG7486

[51] Int. Cl.$^5$ ............................................... A61B 6/00
[52] U.S. Cl. .................................... 128/654; 128/659; 128/203.27
[58] Field of Search ................... 128/654, 659, 203.17, 128/203.27; 600/3

[56] References Cited

PUBLICATIONS

Pusch, "A Test Setup For Inhalation Experiments With Radioactive Aerosols", Atomkernenergie vol. 26 No. 2, pp. 125-128, 1975.
Pusch, "Evaporation Equipment For Producing Radioactive Aerosols", Atomkernenergie vol. 25, No. 2, 1975, pp. 122, 124.

Primary Examiner—Ruth S. Smith
Attorney, Agent, or Firm—Ladas & Parry

[57] ABSTRACT

A diagnostic device, composition and method of diagnosing airway dysfunction in a patient, the apparatus and method require the subjecting of a pharmaceutical acceptable radionuclide, that is the composition, to an elevated temperature in an enclosed spaced to produce an inhalable gas-light product containing the vapour of the radionuclide in the space, delivery of the inhalable gas from the space is governed with the inhalable gas being inhaled by a patient to enable a film to be located adjacent the airways enabling mapping of the deposition of the radionuclide in the airways of the patient's lungs.

10 Claims, 7 Drawing Sheets

DEVICE FOR PRODUCING A GAS-LITE RADIONUCLIDE COMPOSITION

This is a continuation of copending application Ser. No. 07/462,303 filed on Dec. 21, 1989 now abandoned which is a continuation of Ser. No. 07/251,930 filed Sep. 29, 1988 abandoned, which is a continuation of Ser. No. 06/784,847 filed Oct. 4, 1985 abandoned.

The present invention relates to new diagnostic compositions, a method for the production of the compositions and apparatus useful in the production of the compositions.

Ventilation and perfusion imaging of the lungs with radionuclides provides the examination of choice for diagnosing airway dysfunction.

Among the radionuclides there exists very few true gases whose properties may be exploited particularly in the diagnosis of airway dysfunction. The use of radiolabelled krypton and xenon gases to obtain an airway image has a number of practical disadvantages in use as well as diagnostic limitations. Attempts have been made to stimulate gas-like behaviour in the radionuclide $^{99m}$technetium by creating aerosols from Bernoulli-effect nebulizers or an ultra-fine aerosol by burning a flammable solution of $^{99m}$technetium.

Australian Patent No. 521,216 describes a composition comprising a solution containing an alkali metal pertechnetate, such as sodium pertechnetate, in an alcohol such as ethanol. The application describes the use of the composition as a diagnostic aid for lung disorders. The pertechnetate is introduced as an alcoholic aerosol via a propellant or via combustion to result in a suspension of pertechnetate in carbon dioxide, water vapor and air.

Later developments utilise a system to nebulise a technetium solution to obtain a dispersion of particles, having an average particle size of about 0.06 micron radius. Studies on the particles suggest that the compound produced comprises a technetium oxide ($TcO_7$) which is hydrated with two molecules of water. This is consistent with the particle size distribution and other data.

The advantages of such a composition are that the particles can be easily taken into the lung by normal tidal breathing to achieve a good image so that the resultant image reflects a true small airways deposition pattern.

The present invention represents an improvement over the above two methodologies.

The present invention is based on the principle that if a small quantity of a non-volatile pharmaceutically acceptable radionuclide is deposited on a suitable heating means and its temperature is raised above the melting point of the radionuclide, a quantity of the material will be vaporised to produce an inhalable gas-like product.

The present inventor has found that when a suitable radionuclide is used, the vaporised product can be breathed in by a person and the vapor diffuses to the walls of the air sacs (alveoli) and the distribution may be mapped by a gamma camera in the normal manner.

In one form the present invention provides a diagnostic composition comprising a vapor of a non-volatile, pharmaceutically acceptable radionuclide or radioisotope and a pharmaceutically acceptable gaseous diluent. Preferably, the particle size of the radioisotope is about 0.001 microns.

Preferably, the gaseous diluent is an inert gas, such as argon or neon. Alternatively, or additionally, the gaseous diluent may comprise air.

Preferably the radionuclide is a compound of $^{99m}$technetium. The term "radionuclide" refers to the atomic species and therefore includes the element per se or compounds of the radionuclide, such as technetium oxide and technetium carbide. Other suitable radionuclides are $^{125}I$, $^{113m}In$, $^{131}I$ or $^{111}In$.

In another form the present invention provides a method for producing a diagnostic composition suitable in the diagnosis of airway dysfunction comprising subjecting a non-volatile, pharmaceutically acceptable radionuclide to an elevated temperature so that a quantity of the radionuclide is vaporised to produce an inhalable gas-like product.

The invention further provides apparatus which is useful in the production of the diagnostic composition of the present invention. The apparatus comprises a diagnostic device comprising a generally sealed chamber, a mounting located within said chamber, said mounting being adapted to receive a non-volatile radionuclide, heater means to heat said radionuclide to cause at least partial vaporisation thereof so that vapor therefrom is diffused within said chamber, a first duct extending from said chamber through which said vapor may be delivered from within said chamber, and valve means to open and close said first duct to selectively control the delivery of said vapor from said chamber.

In a preferred form of the invention, $^{99m}$technetium is heated in the presence of carbon under a reducing atmosphere, such as in the presence of an inert gas, to elevated temperatures, in the region of at least 1900° C., more preferably to about 2450° C. to produce $^{99m}$technetium carbide vapor.

Alternatively, $^{99m}$technetium may be heated in the presence of oxygen to form $^{99m}$technetium oxide although this will require a higher temperature at which to vaporise, being in the order of 3000° C. Alternatively, $^{99m}$technetium metal itself can be vaporised but again this requires very high temperatures of the order of 3000° C.

When using $^{99m}$technetium, the method of the invention results in particle sizes of about 0.001 microns and these particles, rather than passing through alveoli membranes, adhere to the walls of the alveoli and thus present a relatively true image of respiratory function. Moreover, because the particles tend to adhere to the walls of the alveoli and thus stay in position, there is a longer period before imaging of the patient is essential whereas with the hydrated particles generated by earlier techniques, the particles appear to pass through the alveoli walls in a period of about 12 minutes which means that upon inhalation of these particles, an image had to be taken very promptly. It has been found that with the method of the present invention, the particles appeared to pass through the alveoli walls in a half time of about 25 minutes and that an image should be taken within this period.

In the method of the present invention, the vaporised radionuclide is inhaled by a patient and a gamma camera is used to map the deposition of the radionuclide in the patient's airways. This mapping of the airways produces a picture of the usable airway of the patient and thus can be used to detect airway dysfunction particularly obstructive or restrictive and pulmonary diseases, such as emphysema, pulmonary fibrosis.

The method of the present invention can be used in conjunction with typical perfusion techniques. For example, radio-labelled human serum albumin is ingested by the patient and the labelled protein collects in the arteries around the lung. This perfusion technique can be used to diagnose pulmonary dysfunction. The combination of the ventilation map and the perfusion map allows an accurate picture of airway dysfunction and can be used in particular to diagnose pulmonary embolus.

The present invention, because of its versatility, allows the selection of a number of suitable radionuclides. These include indium-113 m, $^{99m}$technetium as well as Iodine-131. However, $^{99m}$technetium is the preferred radionuclide species.

Both $^{113m}$indium and $^{99m}$technetium are common radionuclides used for diagnostic purposes and are produced free of carrier, and therefore present no toxicity problems with the levels needed to be inhaled by humans. The radiation doses also would be less than that delivered by a normal chest X-ray and for $^{99m}$technetium would be of the same order as that delivered by existing diagnostic techniques.

A preferred form of the apparatus of the present invention will now be described by way of example with reference to the accompanying drawings wherein.

In the accompanying drawings there is schematically depicted a diagnostic device 10 to aid in performing the previously discussed diagnostic method. The device 10 has a base 11 upon which there is mounted a first cover 12. Two further covers 13 and 13a are pivotally mounted on the cover 12 so as to co-operate therewith to selectively enclose the operative portions of the device 10. Mounted on the base 11 is a base plate 14 upon which there is mounted a cylindrical sleeve 15. The sleeve 15 is closed at its upper end by an end cap 16 so that in co-operation with the base plate 14, the sleeve 15 sealingly encompasses a chamber 17. Located on the base plate 14 is a seal 18 which abuts the lower extremity of the sleeve 15. The cylindrical sleeve 15, together with its end cap 16, may be selectively removed from the base plate 14. If so required, catches may be provided so as to clamp the sleeve 15 to the base plate 14.

Figure 1:
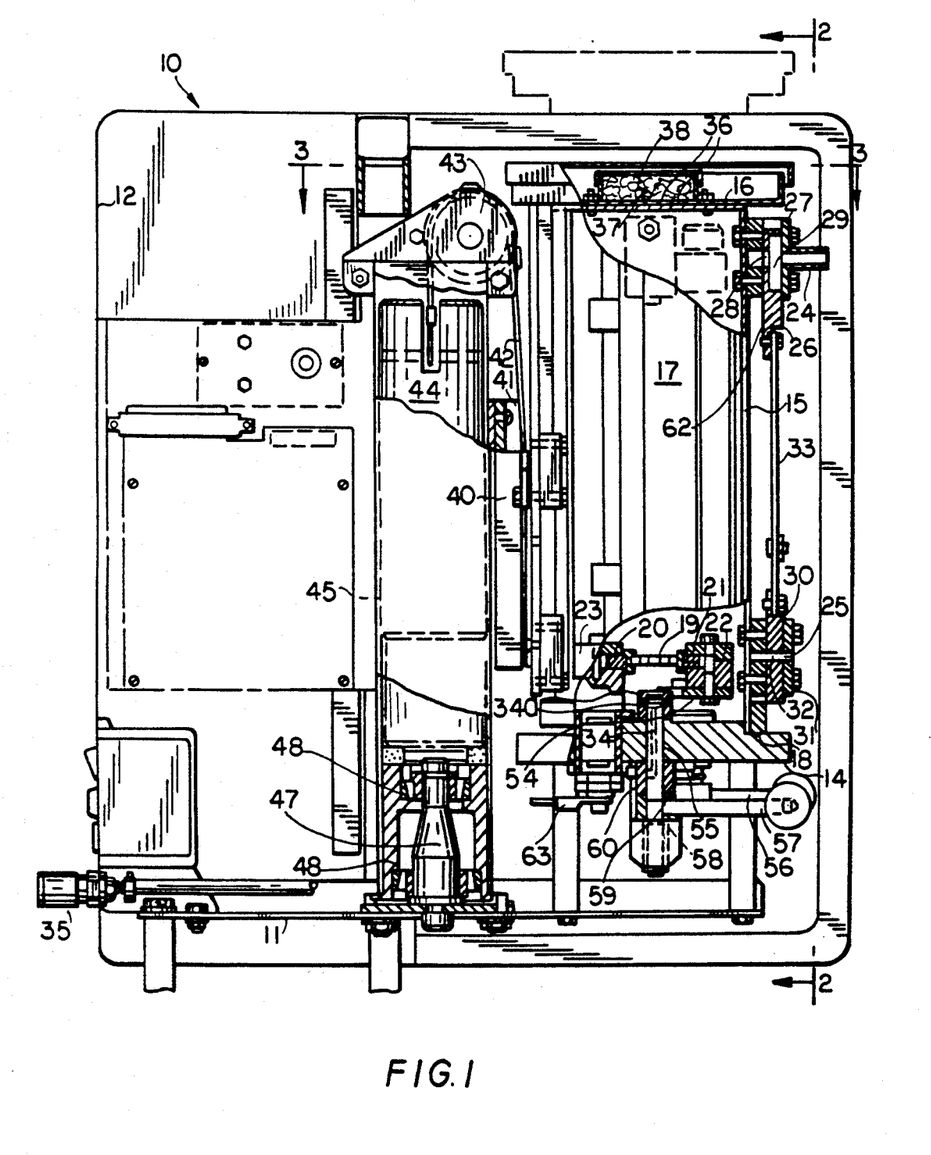
FIG. 1 is a schematic part section side elevation of a diagnostic device.
Figure 2:
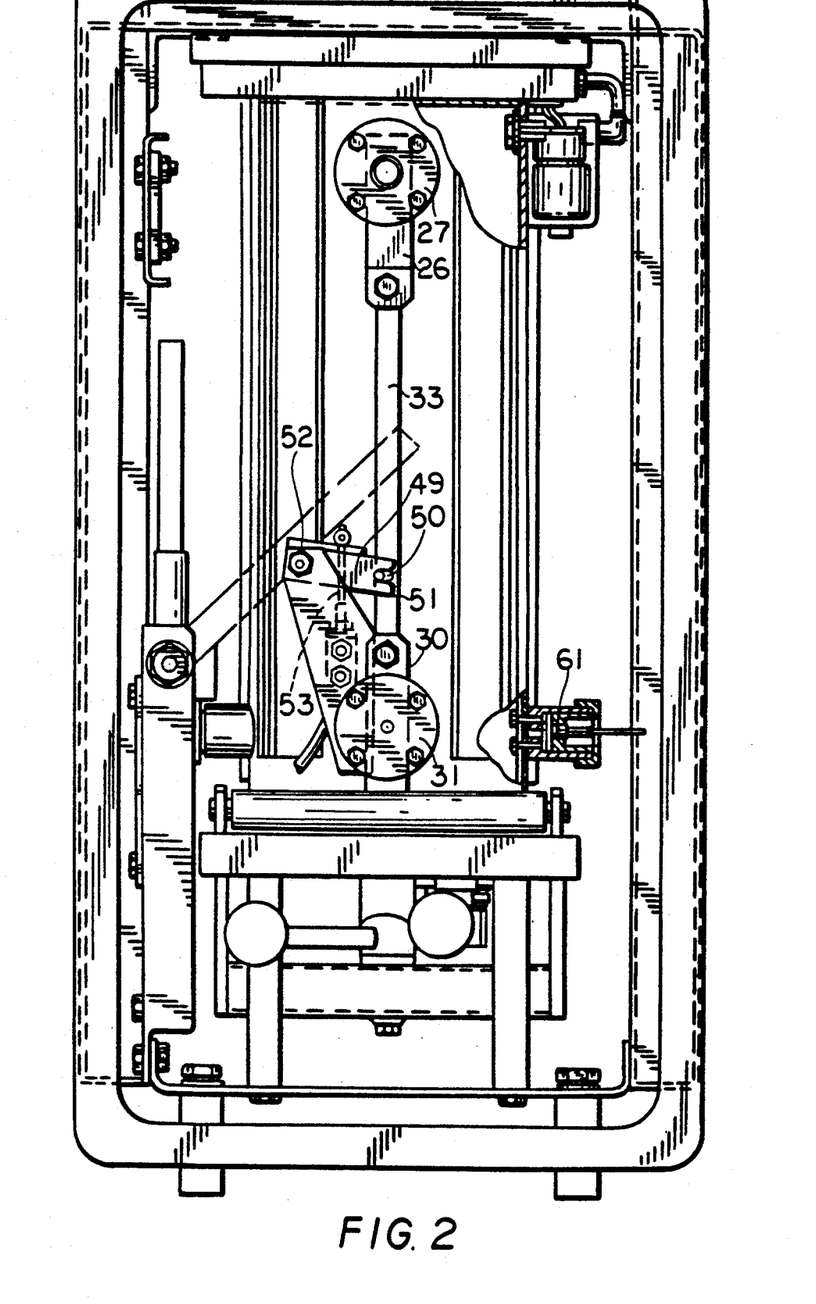
FIG. 2 is a schematic part section end elevation of the device of FIG. 1.
Figure 3:
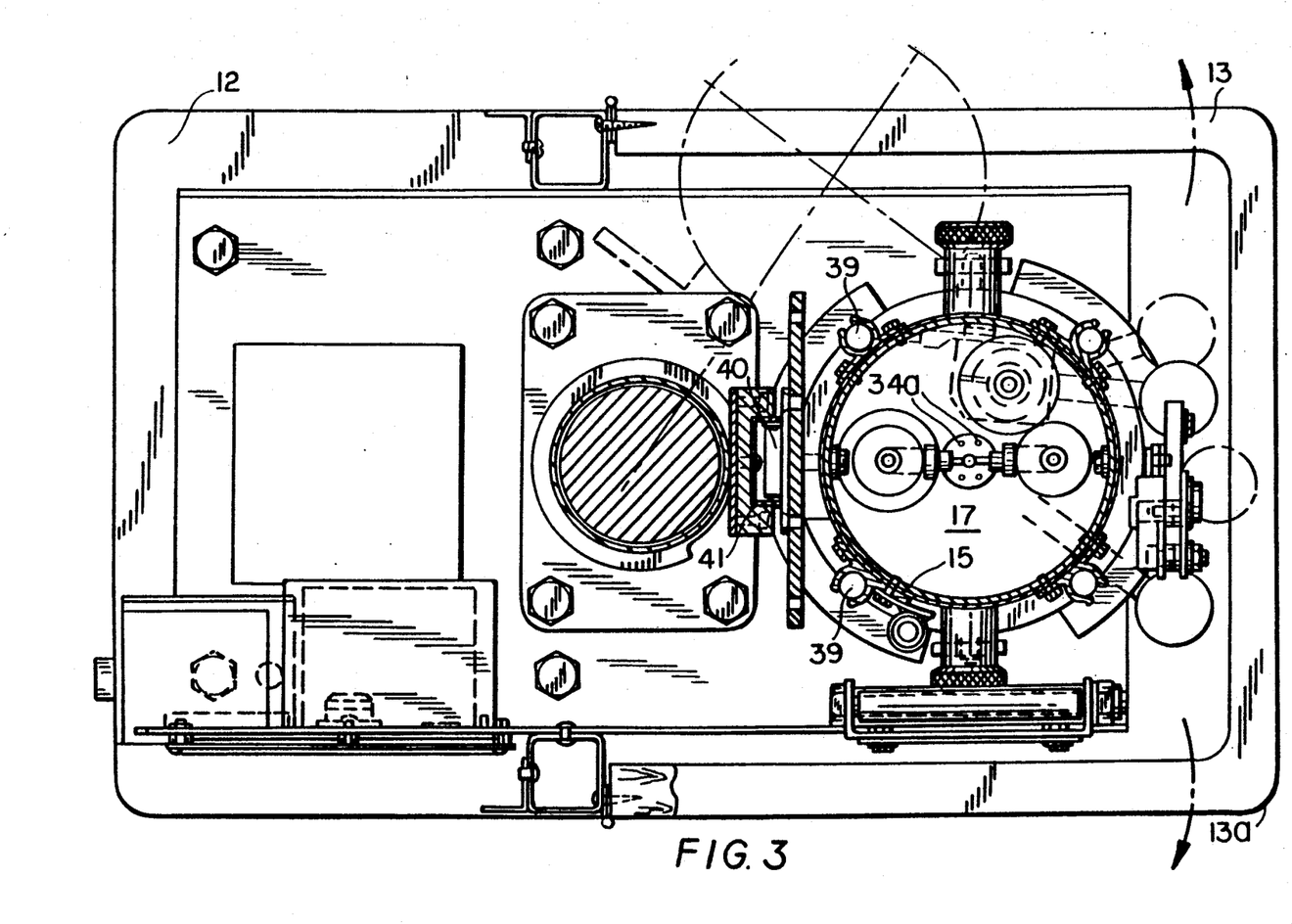
FIG. 3 is a schematic part section top plan view of the device of FIG. 1 sectioned along the line B—B.
Figure 4:
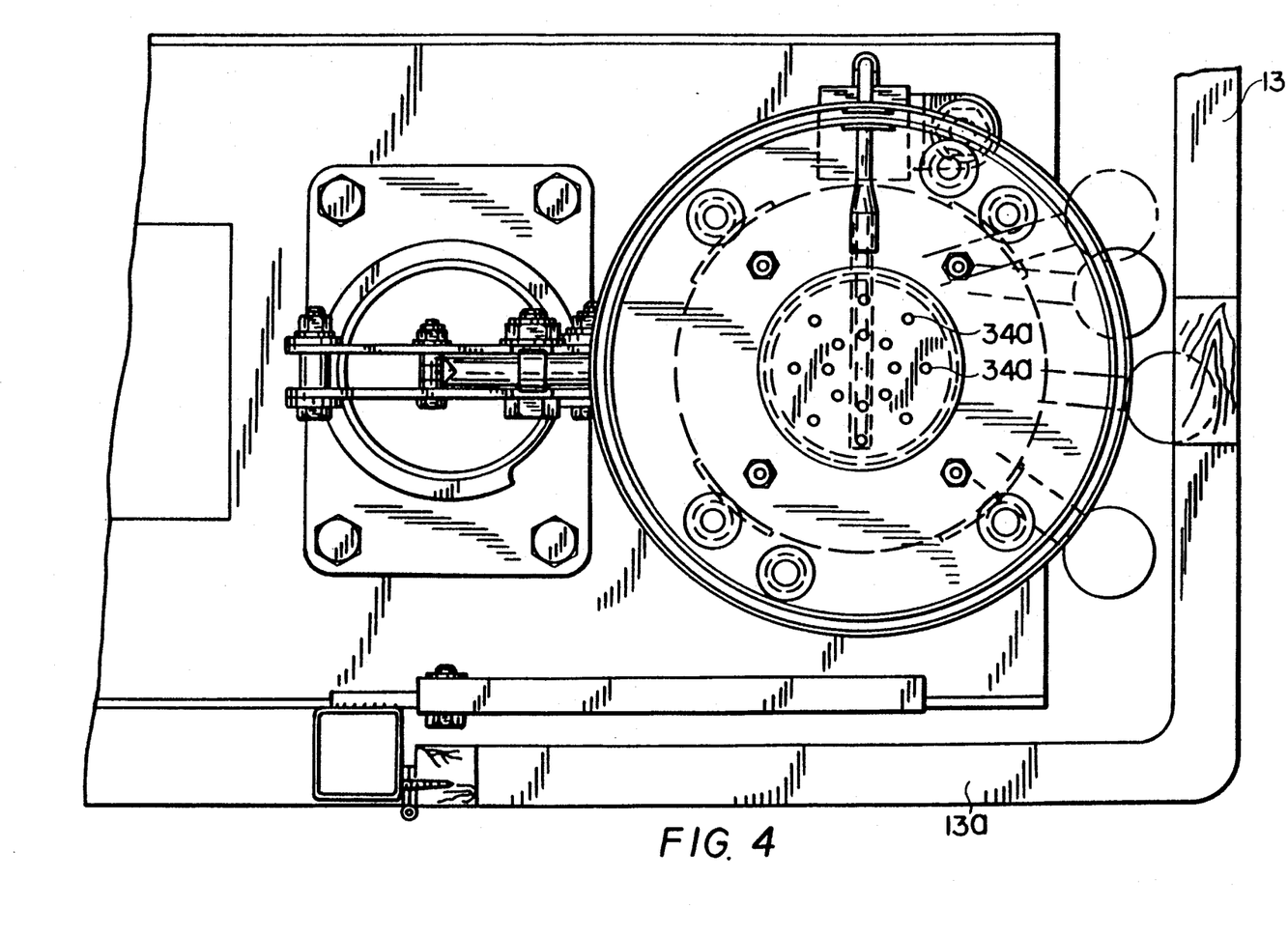
FIG. 4 is a schematic part section top elevation of the device of FIG. 1 sectioned along the line A—A.

Located within the chamber 17 is a carbon crucible 19 extending between two electrodes 20 and 21. The electrodes 20 and 21 are received within electrode mountings 22 and 23, with the electrode mountings 22 and 23 being electrically isolated and being adapted to pass a current by means not shown through the carbon crucible 19 to heat the radionuclide mounted thereon. Extending from the chamber 17 is a first duct 24 located adjacent the upper end of the chamber 17. A second duct 25 also communicates with the chamber 17 adjacent the lower end thereof to allow air to replace the air taken from the chamber 17 by the patient. The duct 24 is selectively closed relative to the chamber 17 by means of a valve member 26 which is slidably mounted in the member 27 which provides the duct 24. The valve member 26 has a closed portion 62 which isolates the duct 24 from the chamber 17 when the valve member 26 is raised. The valve member 26 has an opening 28 which provides for continuity of the duct 24, so that when aligned therewith, vapor located within the chamber 17 may be delivered through the duct 24. The normal operating position of the valve member 26 is depicted in FIG. 1, however it should be appreciated that the valve member 26 can be slidably moved to a position whereat the duct 24 is closed relative to the chamber 17. The valve member 26 is also provided with a cavity 29 which bleeds air into the duct 24, when the duct 24 is closed relative to the chamber 17 to enable the patient to continue to breathe without removing the mouthpiece or mask connected to the duct 24.

The duct 25 is selectively closed by means of a valve member 30 slidably received in the member 31 which provides the duct 25. The valve member 30 is provided with an opening 32 which selectively provides for the continuity of the duct 25.

The valve members 26 and 30 are coupled by a link 33 so that the valve members 26 and 30 are actuated in unison.

Also communicating with the interior of the chamber 17 is a third duct 34 which is connected to a gas fitting 35 by means of a conduit not depicted. The duct 34 enables the selective delivery to the chamber 17 of an inert gas such as argon. The conduit 34 terminates within the chamber 17 with a plurality of nozzles 34a. The end cap 16 is provided with a plurality of apertures 36 which communicate with a bleed passage 37 via a filter 38.

In operation of the abovedescribed device 10, the sleeve 15 is exposed by pivoting the two cover portions 13 and 13a apart. Thereafter the sleeve 15 is removed from the base plate 14 and the carbon crucible 19 placed between the electrodes 20 and 21. The sleeve 15 is then placed back on the base plate 14 so as to provide the generally sealingly closed chamber 17. The valve members 26 and 30 are placed so as to close their respective ducts 24 and 32. The inert gas is then delivered to the chamber 17 and the air bled therefrom via the bleed passage 37. A mouthpiece is connected to the member 27 in order to enable the patient to breath through the passage 24 to inhale air via the cavity 29. This enables the patient to become used to the device 10 prior to actual use. Once the chamber 17 is filled with the inert gas, and the patient is generally ready, a current is delivered to the electrodes 20 and 21 to cause vaporisation of the radionuclide. The vapor then is diffused within the chamber 17. When the patient is ready, the valve members 26 and 30 are moved so that the patient's lungs are now connected to the chamber 17. As the patient continues breathing, the vapors enter the patient's lungs as described previously. This process continues until all the vapor and inert gas are removed from the chamber.

17. As the inert gas and vapor is removed from the chamber 17, air is allowed to be bled into the chamber 17 via the passage 25.

In order to inhibit depositing of the radionuclide on the internal surface of the sleeve 15, heating elements 39 are provided. An electric current is delivered to the heating elements 39 in order to preheat the chamber 17. To facilitate removal of the sleeve 15 from the base plate 14, the sleeve 15 is mounted on a support 40 which is vertically slidably received within a track 41. Extending from the support 40 is a cable 42 which passes over a sheath 43. One extremity of the cable 42 is attached to a counterweight 44 so that the sleeve 15 is easily held in a raised position relative to the base plate 14. The counterweight 44 so that the sleeve 15 is easily held in a raised position relative to the base plate 14. The counterweight 44 is received within a tubular member 45 supported on a bearing member 46. The bearing member 46 is in turn supported on a spigot shaft 47 by means of bearings 48. Accordingly, in operation, the sleeve 15 is moved upward away from the base plate 14 in order to expose the crucible 19. Thereafter the sleeve 15 can be pivoted by use of the bearings 48 to a position whereat the crucible 19 is fully exposed and may be easily removed and replaced. Movement of the sleeve 15 can only take place when the cover parts 13 and 14 are pivoted so as to fully expose the sleeve 15.

Connected to the link 33 in order to facilitate movement thereof is an actuating arm 49 slidably engaging a pin 50 fixed to the link 33. The pin 50 is slidably received within a slot 51 of the arm 49. The arm 49 is pivoted by means of a bolt 52. To cause pivotting movement of the arm 49 a cable 53 is provided which extends to an operator manipulable lever external of the cover 12.

To facilitate easy replacement of the crucible 19, the mounting 22 is supported on a rotatable arm 54 fixed to a shaft 55. The arm 54 is caused to pivot via rotation of the shaft 55 upon actuation of the lever 56. To clamp the shaft 55 in a required position, a further lever 57 is attached to a clamp member 58 which has a cam surface 59. The cam surface 59 co-operates with a further cam surface 60 fixed to the shaft 55. Upon rotation of the cam surface 59 via operation of the lever 57, the shaft 55 may be clamped to the base plate 14.

To ensure that the radionuclide reaches the temperature necessary for vaporisation, a sensor 61 is directed at the crucible 19. The sensor 61 is a photosensitive transistor which is connected to a control circuit which controls the delivery of current to the electrode 20 and 21.

Figure 5:
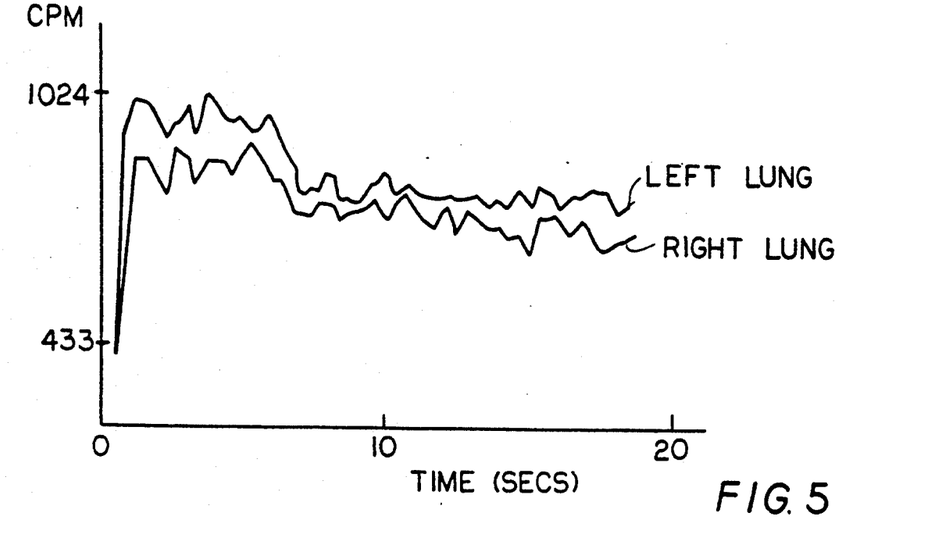
FIG. 5 is a graph showing the amount of $^{99m}$technetium vapor inhaled and the rate at which it is inhaled into the airways of a patient.

Turning now to FIG. 5, the rate at which the lungs fill is represented by the counts detected in the right lung and left lung of a patient after inhalation of $^{99m}$technetium carbide vapor produced in accordance with the present invention. The patient inhaled the vapor and then held his breath for a period of 20 seconds which allows deposition of the labelled species on the alveoli walls. In contrast, if the patient had exhaled immediately, there would have been a relatively sharp drop in CPM. Thus, the patient should inhale and hold for as long as possible to ensure adequate deposition of the labelled species onto the walls of the airways and thus facilitate an adequate deposition pattern.

Figure 6:
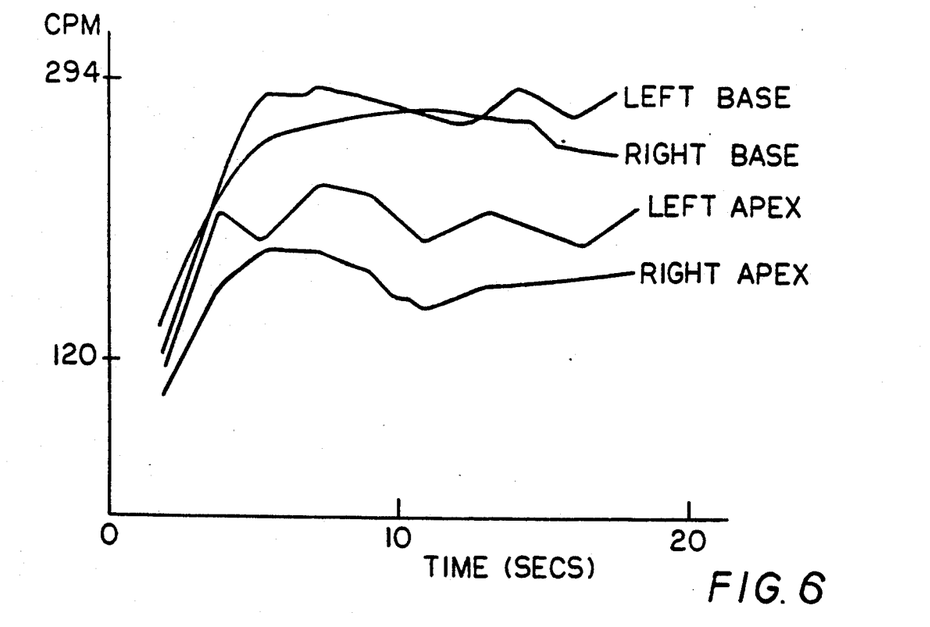
FIG. 6 is a graph showing the amount of $^{99m}$technetium vapor inhaled into and deposited on the different areas of the lungs.

FIG. 6 maps the distribution of $^{99m}$technetium carbide over a period of time from inhalation in a patient who is either standing or sitting upon inhalation and mapping. It can be seen from FIG. 6 that there is a higher count of the radionuclide in the base of both lungs as compared to the apex. The radionuclide tends to fall to the lower part of the lung when the patient is standing. Preferably, the patient should be supine when inhaling and mapping in accordance with the present invention.

Figure 7:
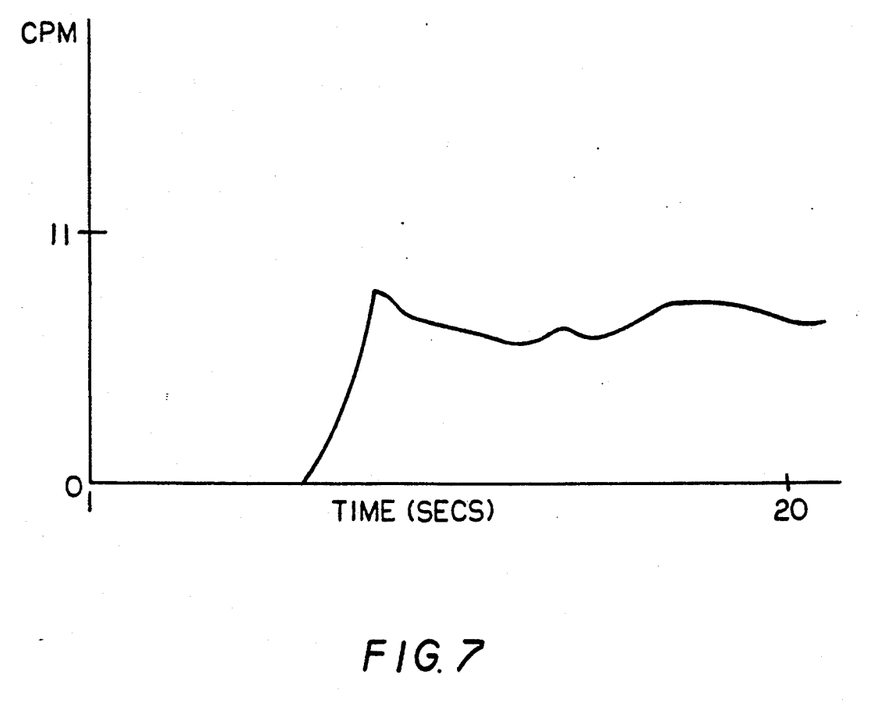
FIG. 7 shows the distribution of counts of $^{99m}$technetium in the region of the filament in the apparatus of the invention.

FIG. 7 graphs the counts and thus the radionuclide vapor in the area of the filament (heating means) in the apparatus of the present invention. The count rate starts to increase as the filament heats to a temperature at which the radionuclide vaporises and comes off the filament. Although not shown in the Figure, counts would begin to fall after significant amounts of the species had been vaporised from the heating means and released from the chamber or inhaled by the patient.

Figure 8A:
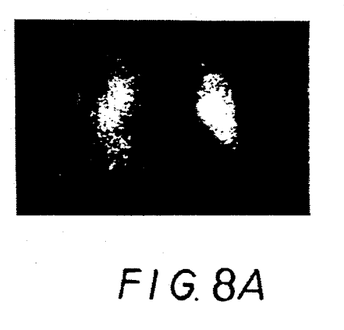
FIGS. 8A and 8B are gamma camera photographs of a patient's lungs after ventilation of the airways in accordance with the present invention and FIGS. 8C and 8D are gamma photographs of the same lungs after ventilation and perfusion as described hereinafter.
Figure 8B:
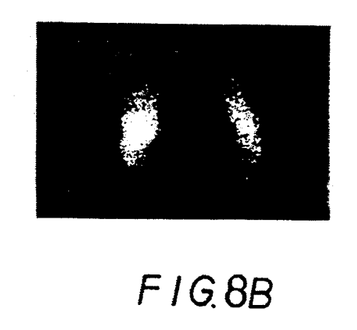

Turning to FIGS. 8A and 8B, there is shown a gamma camera photograph of a patient's lungs upon inhalation of $^{99m}$technetium carbide vapor produced in accordance with the present invention. FIG. 8A is an anterior view of the lungs and FIG. 8B is a posterior view of the lungs. In FIG. 8A, the left lung which is on the lefthand side of the photograph, can be seen to be slightly smaller due to the blocking effect of the heart on the mapping of the $^{99m}$Te deposition. In the posterior view, FIG. 8B, the lefthand lung appears on the righthand side of the photograph.

The deposition of $^{99m}$Te in the airways gives a picture of the usable airway to the skilled diagnostician. The ventilation pattern of the lungs shown in FIGS. 8A and 8B does not indicate obstruction of the airways although the pattern of ventilation does not indicate the airways to be in good condition.

Figure 8C:
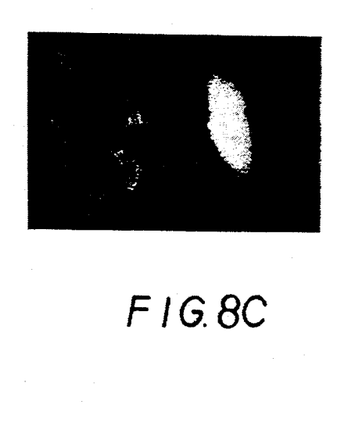
Figure 8D:
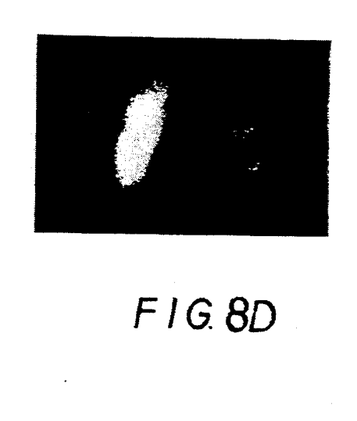

In FIGS. 8C and 8D, a perfusion pattern of the lungs is shown. The patient ingests a suitably radio-labelled human serum albumen which accumulates in the blood vessels surrounding the lungs. A gamma camera then maps the distribution of the radio labelled species in the same manner as a deposition pattern is mapped after ventilation of the diagnostic composition of the present invention. FIG. 8C represents the anterior view of the lungs after perfusion and FIG. 8D is a posterior view of the lungs after perfusion. It can be seen that the right lung has significantly less counts of the radio labelled species and thus multiple defects in perfusion to the right lung. This suggests a high probability of pulmonary embolism in the arteries of the right lung.

The combination of the ventilation technique in accordance with the present invention together with a perfusion technique provides the diagnostician with an accurate picture of the airways and aids the diagnostician in ascertaining airway dysfunction. In the absence of an accurate ventilation pattern, perfusion diagnoses can be misleading. Therefore, not only does the technique of the present invention aid in the detection of ventilation defects such as obstruction, growth or loss of function in certain areas of the lungs, but it also aids in more accurately diagnosing pulmonary dysfunction.

In typical clinical trials, such as the one resulting in FIGS. 8A and 8B, 5.0 mCi of $^{99m}$ technetium in the form of technetium pertechnetate is placed in the carbon crucible of the apparatus of the present invention and the crucible is heated to a temperature of about 2400° C. The resulting $^{99m}$technetium carbide is inhaled by the patient from the apparatus and subsequently a gamma camera photograph is taken of the lungs both from the front and back. The resulting photograph provides a ventilation pattern of the patient's airways as described above.

What I claim is:

1. A device for producing a gas-like radionuclide composition from a non-volatile radionuclide, said composition including carbon and said radionuclide, said device comprising:
   a sealable chamber;
   a mounting structure within the sealable chamber;
   a carbon substrate mounted on said mounting structure and bearing a non-volatile radionuclide;
   means for heating said substrate to an elevated temperature to produce said gas-like composition, wherein said elevated temperature is less that the vaporization temperature of the non-volatile radionuclide;
   a first duct extending from the interior of the chamber, the first duct adapted for receiving a mouthpiece; and
   a first valve co-operating with the first duct for opening and closing said first duct.

2. The device of claim 1, wherein:
   said carbon substrate is a carbon crucible.

3. The device of claim 2, wherein:
   the mounting structure further comprises electrodes adapted for holding said carbon crucible.

4. The device of claim 3, wherein the sealable chamber further comprises a second duct and a second valve co-operating with the second duct;
   the second duct extending from the interior of the chamber to the atmosphere;
   the second valve operatively engaged with said first valve, so they are operable, in unison, from an open state to a closed state.

5. The device of claim 4, wherein:
   the sealable chamber further comprises a third duct and a bleed passage, the third duct adapted for the delivery of inert gas into the chamber, excess pressure being relieved by the bleed passage.

6. The device of claim 3, wherein:
   the means for heating delivers an electrical current to the mounting structure which heats the non-volatile radionuclide to at least about 2400° C.

7. The device of claim 2, wherein the sealable chamber further comprises a second duct and a second valve co-operating with the second duct;
   the second duct extending from the interior of the chamber to the atmosphere;
   the second valve operatively engaged with said first valve, so they are operable, in unison, from an open state to a closed state.

8. The device of claim 2, wherein:
   the means for heating delivers an electrical current to the mounting structure which heats the non-volatile radionuclide to at least about 2400° C.

9. The device of claim 1, wherein the sealable chamber further comprises a second duct and a second valve co-operating with the second duct;
   the second duct extending from the interior of the chamber to the atmosphere;
   the second valve operatively engaged with said first valve, so they are operable, in unison, from an open state to a closed state.

10. The device of claim 1, wherein:
    the means for heating delivers an electrical current to the mounting structure which heats the non-volatile radionuclide to at least about 2400° C.

* * * * *